United States Patent
Kelly et al.

(10) Patent No.: US 10,140,423 B2
(45) Date of Patent: Nov. 27, 2018

(54) MODIFYING CHARACTERISTICS OF A MEDICAL DEVICE UTILIZING A MOBILE DEVICE

(71) Applicant: CERNER INNOVATION, INC., Kansas City, KS (US)

(72) Inventors: Lisa Kelly, Overland Park, KS (US); Judith A. Zakutny, Olathe, KS (US); Bryan Muehlmeier, Overland Park, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 511 days.

(21) Appl. No.: 14/841,110

(22) Filed: Aug. 31, 2015

(65) Prior Publication Data

US 2017/0061097 A1   Mar. 2, 2017

(51) Int. Cl.
*G16H 10/60* (2018.01)
*G06F 19/00* (2018.01)

(52) U.S. Cl.
CPC ......... *G06F 19/3468* (2013.01); *G16H 10/60* (2018.01); *A61M 2205/18* (2013.01); *A61M 2205/35* (2013.01)

(58) Field of Classification Search
CPC ... G06F 19/3468; G06F 19/325; G06Q 50/22; G16H 10/60; A61M 2205/18; A61M 2205/35
USPC ......................................................... 705/2–3
See application file for complete search history.

(56) References Cited

U.S. PATENT DOCUMENTS

2005/0144043 A1* 6/2005 Holland ................ G06F 19/326
                                                              705/3
2007/0040692 A1* 2/2007 Smith ................... A61B 5/1115
                                                              340/573.1

* cited by examiner

*Primary Examiner* — Joy Chng
(74) *Attorney, Agent, or Firm* — Shook, Hardy & Bacon, L.L.P.

(57) ABSTRACT

Methods, computer systems and computer readable media for modifying characteristics of a medical device via a mobile device are provided. In embodiments, data communicated by an infusion device providing an infusion to a patient is provided to a mobile device associated with a clinician. A notification associated with the infusion device is received and communicated to the mobile device. Confirmation of the notification is received from the clinician via the mobile device and the notification is communicated to the infusion device. Characteristics of the infusion are automatically modified in accordance with the notification.

18 Claims, 4 Drawing Sheets

MODIFYING CHARACTERISTICS OF A MEDICAL DEVICE UTILIZING A MOBILE DEVICE

BACKGROUND

Infusion pumps infuse fluids, medications and/or nutrients into the circulatory system of an individual or patient. The infusions may be intravenous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like.

In many cases, various characteristics of a medical device, such as an infusion device, need to be modified. Although an order may be entered that includes such modifications, current infusion devices require another clinician to be physically present at the device and manually make changes on the device to download the modifications to the device. This causes delays in providing the patient the modifications. In other cases, alarms may be provided by the medical devices that create nuisances for patients, family, and clinicians alike. For example, the clinician may be in the same room as the device and already aware of an issue. However, current devices still provide alarms that have to be manually silenced by the clinician.

SUMMARY

Embodiments of the present invention are generally directed to methods, computer systems and computer readable media for modifying characteristics of a medical device via a mobile device. Data communicated by the device is provided to a mobile device. If a notification (e.g., modification to an order, a change to a suggested protocol, or an alarm associated with the device) is received, such as from an electronic medical record (EMR), a healthcare application, or the like, it is provided to the mobile device. Upon confirming the notification via the mobile device, the notification is communicated to the medical device. Characteristics (e.g., rate of infusion, dosage, bolus, alarm suppression) of the medical device are automatically modified in accordance with the notification.

Accordingly, in one aspect, an embodiment of the present invention is directed to one or more computer storage media storing computer-useable instructions that, when used by one or more computing devices, cause the one or more computing devices to perform operations. The operations include providing, at a mobile device associated with a clinician, data communicated by an infusion device providing an infusion to a patient. The operations also include receiving a notification associated with the infusion device. The operations further include receiving a confirmation of the notification from the clinician via the mobile device. The operations also include communicating the notification to the infusion device. The operations further include automatically modifying characteristics of the infusion in accordance with the notification.

In another embodiment, an aspect is directed to a computer-implemented method in a clinical computing environment. The method includes providing, via a first computing process, a notification at a mobile device, the notification being associated with an infusion device. The method also includes receiving, via a second computing process, a confirmation of the notification from the clinician, the confirmation being communicated to an electronic medical record associated with a patient receiving an infusion from the infusion device. The method further includes communicating, via a third computing process, the notification from the EMR to the infusion device. The method also includes automatically modifying, via a fourth computing process, characteristics of the infusion in accordance with the notification. Each computing process is performed by one or more computing devices.

A further embodiment is directed to a system comprising: one or more processors; and one or more computer storage media storing instructions that, when used by the one or more processors, cause the one or more processors to: provide a notification at a mobile device, the notification being associated with an infusion device; receive a confirmation of the notification from the clinician, the confirmation being communicated to an electronic medical record (EMR) associated with a patient receiving an infusion from the infusion device; communicate the notification from the EMR to the infusion device; and automatically modify characteristics of the infusion in accordance with the notification.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As mentioned above, in many cases, various characteristics of a medical device, such as an infusion device, need to be modified. Although an order may be entered that includes such modifications, current infusion devices require another clinician to be physically present at the device and manually make changes on the device to download the modifications to the device. This causes delays in providing the patient the modifications. In other cases, alarms may be provided by the medical devices that create nuisances for patients, family, and clinicians alike. For example, the clinician may be in the same room as the device and already aware of an issue. However, current devices still provide alarms that have to be manually silenced by the clinician.

Embodiments of the present invention are generally directed to methods, computer systems and computer readable media for modifying characteristics of a medical device via a mobile device. Data communicated by an infusion device providing an infusion to a patient is provided to a mobile device associated with a clinician. A notification associated with the infusion device is received and communicated to the mobile device. A confirmation of the notification is received from the clinician via the mobile device. The notification is communicated to the infusion device and characteristics of the infusion are automatically modified in accordance with the notification.

Figure 1:
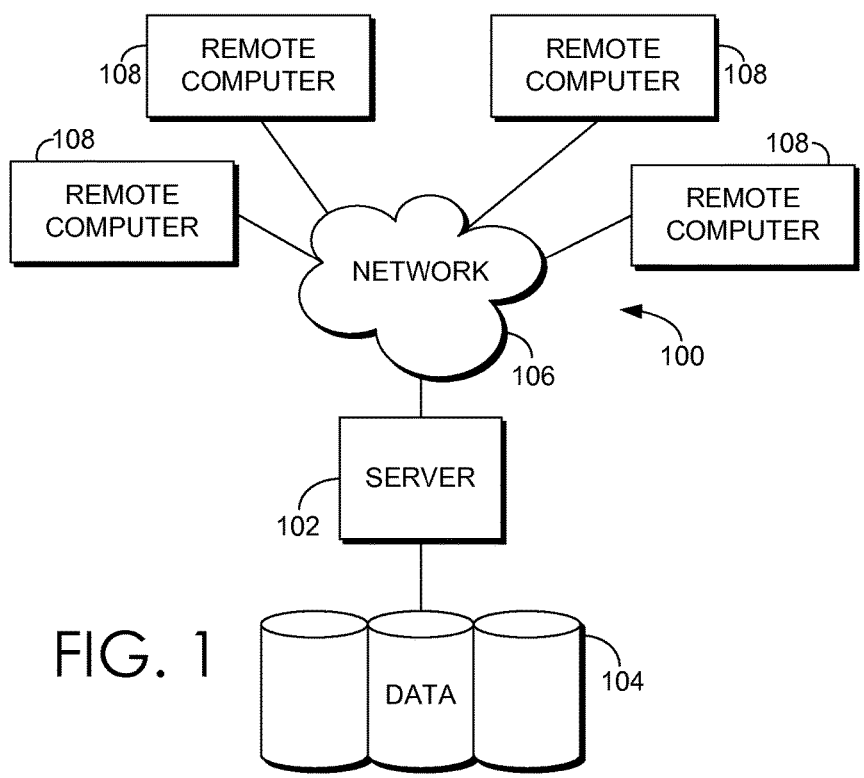
FIG. 1 is a block diagram of an exemplary computing environment suitable to implement embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, students, office assistants and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
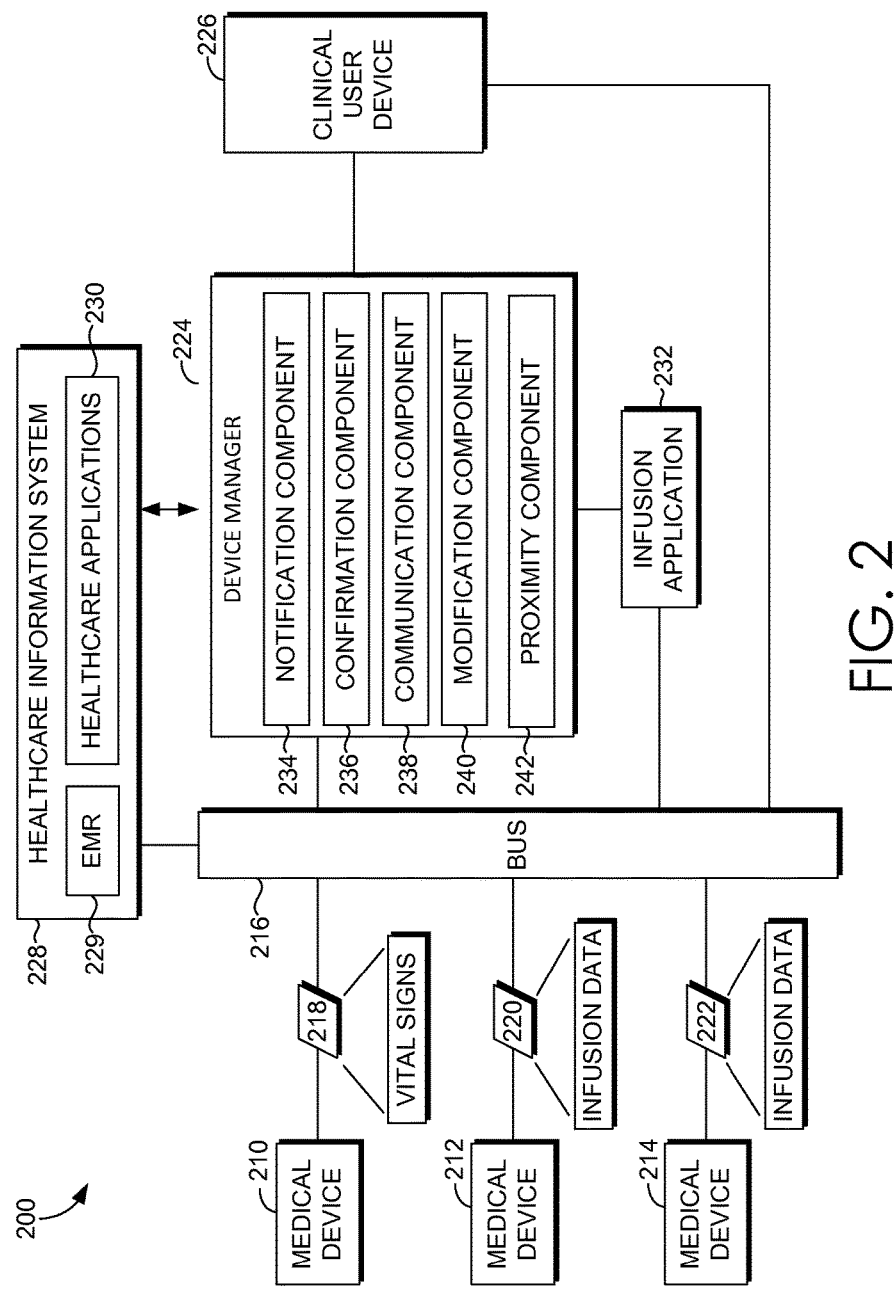
FIG. 2 is an exemplary system architecture suitable to implement embodiments of the present invention.

Turning now to FIG. 2, a schematic diagram depicts an operating environment, identified generally by reference numeral 200, suitable to practice an embodiment of the present invention. FIG. 2 includes various components that communicate with one another, including medical device 210, infusion pump devices 212 and 214, clinical user devices 226, bus 216, device manager 224, healthcare information system 228 and infusion application 232. In one embodiment of the present invention, data generated by a medical device 210 or an infusion pump device 212, and 214 is routed to and managed by device manager 224, as opposed to, each medical device 210 and infusion pump device 212 displaying information on the medical device or infusion pump respectively. For example, data 218, 220, and 222 is communicated to bus 216, which might then forward the data to device manager 224 to be further processed and routed. Before describing in more detail how these components communicate, each component will be generally described.

In an embodiment of the present invention, medical device 210 might include cardiac monitors, ventilators, balloon pumps, patient beds, sequential-compression devices, electronic security devices, and vital-sign detecting devices. Medical device 210 may generate various data (e.g., measured heart rate) that, as described in more detail below, is communicated to other components (e.g., bus 216) of operating environment 200. Moreover, medical device 210 might also receive information from components of operating environment 200.

In another embodiment of the present invention infusion pumps 212 and 214 infuse fluids, medications and/or nutrients into the circulatory system of an individual or patient. The infusions may be, but are not limited to, intravenous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like. The fluid, medication and/or nutrients are typically contained in an infusion container, such as an infusion bag. It will be appreciate that any type container may be utilized to hold the infusion fluid, medication and/or nutrients. Infusion pumps 212 and 214 generate various data, including, but not limited to, remaining volume of infusion (e.g., amount remaining in fluid container), rate of infusion (e.g., how fast fluid is being infused), alerts (e.g., air in line, maintenance of pump needed, high backpressure, low infusion, occlusion, or pump stopped). This data is communicated to other components (e.g., bus 216) of operating environment 200. Moreover, infusion pumps 212 and 214 might also receive information from components of operating environment 200.

Healthcare information system 228 includes an integrated system of healthcare-related information that is usable by a healthcare facility to operate and provide patient care. For example, healthcare information system 228 includes an electronic medical record 229 (also referred to herein as "EMR") and a healthcare applications component 230. EMR 229 includes an electronic version of patient records including information for the patient, such as medication and infusion orders, tasks, images, examination reports, testing and lab results, medical history, etc. Healthcare applications component 230 includes information that is input and provided at a patient's point-of-care (e.g., patient bedside) to assist healthcare professionals to provide appropriate care. An exemplary applications component 230 includes a patient order entry component for entering electronic healthcare orders for a patient. In an embodiment of the present invention, healthcare information system 228 receives information from other components, as will be described in more detail below. Moreover, healthcare information system 228 might also provide information that is communicated to other components of operating environment 200.

Clinical user devices 226 include devices that are used within a healthcare facility to receive, display and send information to a user, such as a clinician. Clinician user devices 226 also facilitate requests to receive additional information. Exemplary clinical user devices 226 include personal communication devices. Personal communication devices include devices that are used by an individual to receive and send information, such as an in-house phone or a mobile device. Accordingly, in an embodiment of the present invention, clinical user devices 226 present to users information that is received from other components of operating environment 200. Moreover, clinical user devices 226 might also receive inputs from a clinician that are communicated to other components of operating environment 200. Clinical user devices 226 also communicate to other components of operating environment 200 requests to receive additional information. For example, clinical user device 226 might communicate information to infusion application 232, HIS 228, EMR 229, healthcare application 230, and medical devices 210, 212 and 214.

Infusion application 232 is an electronic application for receiving medication orders, such as infusion orders, to be filled. An exemplary pharmacy system is Cerner Millennium Pharmnet by Cerner Corporation, Kansas City Mo. Typically orders for medications, fluids and nutrients to be filled by a pharmacist are displayed in the pharmacy or pharmacy IV room. The pharmacist can use this information to drive the pharmacy workflow and make sure the necessary medication orders are filled. In another embodiment, infusion application 232 may be an automated pharmacy dispensing system such as Cerner RXStation by Cerner Corporation of Kansas City, Mo. The automated pharmacy system may be an apparatus pre-loaded with medication, fluids and/or nutrients that may be dispensed to fill patient orders.

As previously indicated, and as depicted in FIG. 2, each of medical devices 210, infusion pumps 212 and 214, healthcare information system 228, device manager 224, clinical user devices 226 and infusion application 232 may be in communication with bus 216. Bus 216 generally provides a connection framework for these components by creating and managing all connections, providing a messaging architecture to facilitate an exchange of information between the various components of FIG. 2, and providing general operational and management capabilities for connected devices. In one embodiment, medical device 210, infusion pumps 212 and 214, device manager 224, clinical user devices 226, healthcare information system 228 and infusion application 232 communicate with bus 216 as described in U.S. patent application Ser. No. 12/347,475 (U.S. Pat. App. '475), which is incorporated herein by reference. For example, infusion pumps 212 and 214 might include various different types of infusion pumps that are manufactured by various different vendors. As such, components of FIG. 2 might communicate with bus 216 via a gateway (e.g., device gateway or internal gateway), an adapter, or by any other means described by U.S. Pat. App. '475. In a further embodiment, bus 216 includes those capabilities described in U.S. Pat. App. '475. As indicated in U.S. Pat. App. '475, once data is received (e.g., data 218, 220, and 222) it can be sorted and routed to other applications.

In an embodiment of the present invention, such applications are included in a device manager 224. As such, bus 216 might receive information (e.g., data 218, 220, and 222) and route the data to device manager 224. Moreover, bus 216 might receive information from clinical user devices 226 and route the information to device manager 224. In a further embodiment, bus 216 receives information from healthcare information system 228 and routes the information to device manager 224. In another embodiment, bus 216 receives information from device manager 224 and routes the information to other components. For example, bus 216 routes information from clinical user devices 226 to healthcare information system 228.

In an embodiment of the present invention, device manager 224 communicates with bus 216 and functions to facilitate the management and control of the medical devices 210, 212, 214 based on information received from the various components of operating environment 200 (e.g., orders modifications, protocols, alarms, etc.) via clinical user devices 226. In this way, a clinician is able to use a clinical user device 226 to confirm order modifications, protocols, or silence alarms. For example, information form a medical device 210 may indicate that a characteristic (e.g., dosage, rate, etc.) of an infusion should be modified. A clinician seeing this information may order the necessary modification, such as via the EMR 229, healthcare application 230, or infusion application 232. Upon entering the order, instead of another clinician having to physically be at one of the medical devices 210, 212, 214 to program the device, that clinician may confirm the order utilizing the clinical user device 226. The device is then programmed with the appropriate modification and begins treating the patient in a much more timely fashion.

Device manager 224 includes notification component 234, confirmation component 236, communication component 238, modification component 240, and proximity component 242. While these components are included in the embodiment of FIG. 2, any number of components, either more or less than the illustrated components, may be used to accomplish the purposes of the present invention. Other components and subcomponents are contemplated to be within the scope of the present invention. Furthermore, although depicted as residing on one device, such as a server, it will be appreciated that any number of components and/or subcomponents may reside on any number of computing devices or servers.

Notification component 234 is generally configured to receive notifications associated with medical devices 210, 212, 214. In some embodiments, the notification is associated with an infusion device. The notifications may include a modification to an order associated with the medical device. For example, a clinician may have received information from one or more of the medical devices 210, 212, 214 indicating an infusion order for a patient should be modified. Similarly, the clinician may have received information from the EMR 229 indicating the infusion order should be modified. In either scenario, the clinician may enter the modification into the EMR 229, a healthcare application 230, or infusion application 232. Once entered, notification component 234 receives the modification and communication component, discussed in more detail below, communicates the notification to the clinician via a clinical user device 226 (e.g., a mobile device).

Confirmation component 236 is generally configured to receive confirmation of the notification from the clinician via a clinical user device 226. Accordingly, the clinician is able to quickly and efficiently confirm a modification to an order, change the device to incorporate or utilize a suggested protocol, or silence an alarm on the device without being physically in the same location as the medical device 210, 212, 214. In this way, the clinician manages and controls the medical devices 210, 212, 214 utilizing the clinical user device 226 and can do so from any location. In some embodiments, the confirmation is communicated to the EMR associated with the patient receiving an infusion from an infusion device.

Communication component 238 is generally configured to communicate the notification to the medical device. This enables the confirmation received from the clinical user device 226 via the confirmation component 236 to cause the medical device to program down the notification. In this way, the medical device receives the modification to the order or suggested protocol from the EMR 229, healthcare application 230, or infusion application 232, in various embodiments.

Modification component 240 is generally configured to alter the functioning of the medical device in accordance with the notification. For example, characteristics of an infusion are automatically modified in accordance with the notification. As such, a clinician, by confirming a notification via the clinical user device 226, can control the functionality of the medical devices 210, 212, 214. In some embodiments, an infusion is automatically modified in accordance with the notification.

In embodiments, proximity component 242 is generally configured to detect that the clinical user device 226 is in proximity to the medical device (e.g., infusion device). For example, the proximity component 242 may detect that the clinical user device 226 is located in the same room or physical location as the infusion device. If the infusion device is generating some type of alarm that might nuisance a sleeping patient or a clinician that is already aware of an issue causing the alarm because the clinician is physically near the infusion device, there is no need to generate an audible alarm. Because proximity component 242 detects the presence of the clinician user device, proximity component 242 automatically suppresses the alarm associated with the infusion device. Although the alarm is suppressed, data associated with the alarm may still be communicated by proximity component 242 to the EMR associated with the patient.

Figure 3:
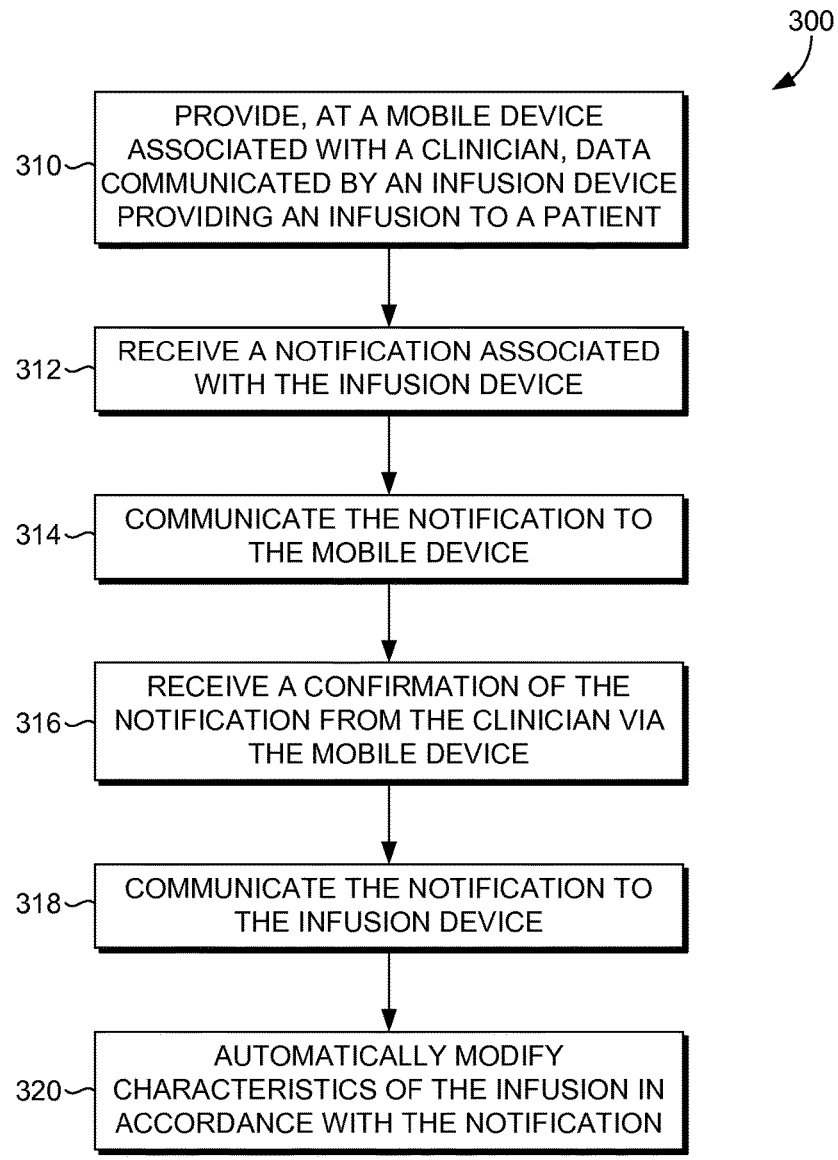
FIG. 3 is a flow diagram showing a method for modifying characteristics of a medical device in accordance with embodiments of the present invention.

Turning now to FIG. 3, a flow diagram is provided that illustrates a method 300 for modifying characteristics of a medical device, in accordance with embodiments of the present invention. At step 310, data communicated by an infusion device providing an infusion to a patient is provided to a mobile device associated with a clinician. The data may include any data displayed on a display of the infusion device itself. At step 312, a notification associated with the infusion device is received. In some embodiments, the notification may include a modification to an order associated with the infusion device. In some embodiments, the notification may be a suggested protocol. In various embodiments, the notification is communicated from the EMR associated with the patient, a healthcare application, an infusion application, and the like.

The notification is communicated to the mobile device, at step 314. A clinician may confirm the notification utilizing the mobile device. A confirmation of the notification is received, at step 316, from the clinician via the mobile device. The notification is then communicated to the infusion device, at step 318. As described above, the notification may be communicated from the EMR associated with the patient, a healthcare application, an infusion application, and the like. In this way, the clinician is able to control the infusion device utilizing the mobile device. Once the notification is communicated to the infusion device, characteristics of the infusion device are automatically modified, at step 320, in accordance with the notification.

In some embodiments, the notification is an alarm associated with the infusion device. In one embodiment, it is detected that the mobile device is in proximity to the infusion device. The alarm associated with the infusion device may be automatically suppressed. Data associated with the alarm is communicated to the EMR associated with the patient.

Figure 4:
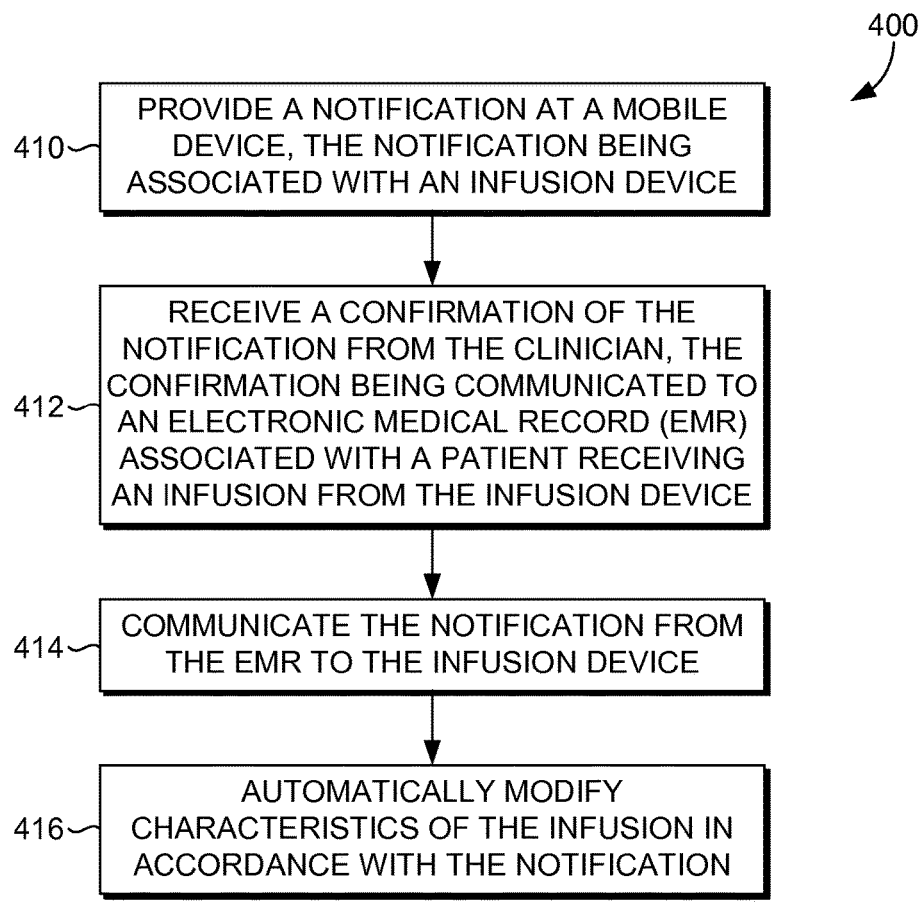
FIG. 4 is a flow diagram showing a method for modifying characteristics of a medical device in accordance with embodiments of the present invention.

With reference now to FIG. 4 a flow diagram is provided that illustrates a method 400 modifying characteristics of a medical device, in accordance with embodiments of the present invention. Initially, at step 410, a notification is provided to a mobile device. The notification is associated with an infusion. In one embodiment, the notification is a modification to an order associated with the infusion device. In one embodiment the notification is a suggested protocol. In one embodiment, the notification is communicated from an EMR associated with the patient, a healthcare application, an infusion application, and the like.

At step 412, a confirmation of the notification is received from the clinician. The confirmation is communicated to an EMR associated with a patient receiving an infusion from the infusion device. The notification is communicated, at step 414, from the EMR to the infusion device. Characteristics of the infusion are automatically modified, at step 416, in accordance with the notification.

In one embodiment, the notification is an alarm associated with the infusion device. The mobile device may be detected to be in proximity of the infusion device (e.g., in the same room, within a certain distance such that an alarm is audible, etc.). The alarm associated with the infusion device may be automatically suppressed. Data associated with the alarm may be communicated to the EMR associated with the patient.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. One or more computer storage media storing computer-useable instructions that, when used by one or more computing devices, cause the one or more computing devices to perform operations comprising:
   receiving a notification from an infusion device, the notification being currently displayed on a display of the infusion device, the infusion device executing at least one previously input order;
   automatically generating at least one suggested course of action in response to the notification;
   communicating the notification and the at least one suggested course of action to a mobile device associated with a clinician;
   receiving an ordered course of action from the clinician via the mobile device, the ordered course of action comprising a modification to at least one characteristic of the infusion device's execution of the previously input order;
   communicating the ordered course of action to the infusion device; and
   automatically modifying the at least one characteristic of the infusion device's execution of the previously input order in accordance with the ordered course of action.

2. The media of claim 1, wherein the ordered course of action is a modification to an order associated with the infusion device.

3. The media of claim 1, wherein the notification is communicated from an electronic medical record associated with the patient.

4. The media of claim 1, wherein the notification is an alarm associated with the infusion device.

5. The media of claim 4, further comprising, detecting that the mobile device is in proximity to the infusion device.

6. The media of claim 5, further comprising automatically suppressing the alarm associated with the infusion device.

7. The media of claim 6, further comprising communicating data associated with the alarm to an electronic medical record associated with the patient.

8. A computer-implemented method in a clinical computing environment comprising:
   providing, via a first computing process, a notification at a mobile device, the notification being associated with an infusion device;
   receiving, via a second computing process, a confirmation of the notification from the clinician, the confirmation being communicated to an electronic medical record (EMR) associated with a patient receiving an infusion from the infusion device;
   communicating, via a third computing process, the notification from the EMR to the infusion device; and
   automatically modifying, via a fourth computing process, characteristics of the infusion in accordance with the notification;
   wherein each computing process is performed by one or more computing devices.

9. The method of claim 8, wherein the ordered course of action is a modification to an order associated with the infusion device.

10. The method of claim 8, wherein the notification is communicated from an electronic medical record associated with the patient.

11. The method of claim 8, wherein the notification is an alarm associated with the infusion device.

12. The method of claim 8, further comprising, detecting, via a fifth computing process, that the mobile device is in proximity to the infusion device.

13. The method of claim 12, further comprising automatically suppressing, via a sixth computing process, the alarm associated with the infusion device.

14. The method of claim 13, further comprising communicating, via a seventh computing process, data associated with the alarm to the EMR associated with the patient.

15. A system comprising:
   one or more processors; and
   one or more computer storage media storing instructions that, when used by the one or more processors, cause the one or more processors to:
   receive a notification from an infusion, the notification being recently displayed on a display of the infusion device, the infusion device executing at least one previously input order;
   automatically generate at least one suggested course of action in response to the notification;
   communicate the notification and the at least one suggested course of action to a mobile device associated with a clinician, a representation of the notification and the at least one suggested course of action configured for display on a display of the mobile device;
   receive an ordered course of action from the clinician via the mobile device, the ordered course of action comprising a modification to at least one characteristic of the infusion device's execution of the previously input order;
   communicate the ordered course of action to the infusion device; and
   automatically modify the at least one characteristic of the infusion device's execution of the previously input order in accordance with the ordered course of action.

16. The system of claim 15, further comprising the one or more computer storage media storing instructions that, when used by the one or more processors, cause the one or more processors to detect that the mobile device is in proximity to the infusion device.

17. The system of claim 16, further comprising the one or more computer storage media storing instructions that, when used by the one or more processors, cause the one or more processors to automatically suppress the alarm associated with the infusion device.

18. The system of claim 17, further comprising the one or more computer storage media storing instructions that, when used by the one or more processors, cause the one or more processors to communicate data associated with the alarm to the EMR associated with the patient.

* * * * *